United States Patent
Liao et al.

(10) Patent No.: US 10,663,763 B2
(45) Date of Patent: May 26, 2020

(54) MULTIFOCAL INTRAOCULAR LENS

(71) Applicant: VISION PRO (WUXI) LTD, Wuxi (CN)

(72) Inventors: Xiugao Liao, Wuxi (CN); Zhenyu Feng, Wuxi (CN); Jinghui Cao, Wuxi (CN); Qin Yang, Wuxi (CN)

(73) Assignee: VISION PRO (WUXI) LTD, Wuxi (CN)

( * ) Notice: Subject to any disclaimer, the term of this patent is extended or adjusted under 35 U.S.C. 154(b) by 102 days.

(21) Appl. No.: 16/048,374

(22) Filed: Jul. 30, 2018

(65) Prior Publication Data
US 2019/0004334 A1 Jan. 3, 2019

Related U.S. Application Data

(63) Continuation-in-part of application No. PCT/CN2017/109294, filed on Nov. 3, 2017.

(30) Foreign Application Priority Data

Jul. 12, 2017 (CN) .......................... 2017 1 0566074

(51) Int. Cl.
*G02C 7/06* (2006.01)
*G02B 27/00* (2006.01)
(Continued)

(52) U.S. Cl.
CPC .............. *G02C 7/06* (2013.01); *A61F 2/1618* (2013.01); *G02B 9/34* (2013.01); *G02B 27/0037* (2013.01);
(Continued)

(58) Field of Classification Search
CPC ......... G02C 7/06; G02B 9/34; G02B 27/0037
See application file for complete search history.

(56) References Cited

U.S. PATENT DOCUMENTS

| 4,409,691 A | 10/1983 | Levy |
| 4,997,442 A | 3/1991 | Barrett |

(Continued)

FOREIGN PATENT DOCUMENTS

| CN | 101422392 A | 5/2009 |
| CN | 204293311 U | 4/2015 |

(Continued)

*Primary Examiner* — Jack Dinh
(74) *Attorney, Agent, or Firm* — Bayramoglu Law Offices LLC

(57) ABSTRACT

The present invention is a multifocal intraocular lens including an optical body, a first support loop and a second support loop, wherein, the optical body is composed of a substrate layer and a coating layer; the substrate layer, the first support loop and the second support loop have a one-piece structure and are formed integrally with the same material; the coating layer is cemented on the substrate layer by means of injection-compression molding; the substrate layer and the coating layer are made of different materials. The optical body of the present invention is a multifocal optical zone with a double-cemented structure. The optical zone includes a plurality of binary surfaces and an aspheric surface, effectively correcting chromatic aberration of the secondary spectrum, improving image quality, expanding the range of additional optical power, and achieving a full range of vision.

10 Claims, 7 Drawing Sheets

(51) Int. Cl.
*G02B 9/34* (2006.01)
*A61F 2/16* (2006.01)
*G02C 7/04* (2006.01)

(52) U.S. Cl.
CPC ...... *A61F 2002/1681* (2013.01); *G02C 7/042* (2013.01); *G02C 2202/20* (2013.01)

(56) References Cited

U.S. PATENT DOCUMENTS

| | | |
|---|---|---|
| 5,217,491 A | 6/1993 | Vanderbilt |
| 5,496,366 A | 3/1996 | Cumming |
| 5,674,282 A | 10/1997 | Cumming |
| 6,178,878 B1 | 1/2001 | Haas |
| 6,197,059 B1 | 3/2001 | Cumming |
| 6,387,126 B1 | 5/2002 | Cumming |
| 6,406,494 B1 | 6/2002 | Laguette et al. |
| 2010/0318186 A1* | 12/2010 | Bumbalough ........ A61F 2/1613 623/6.43 |

FOREIGN PATENT DOCUMENTS

| | | |
|---|---|---|
| CN | 204428208 U | 7/2015 |
| CN | 106667623 A | 5/2017 |
| CN | 107212949 A | 9/2017 |
| EP | 2548533 A1 | 1/2013 |

* cited by examiner

MULTIFOCAL INTRAOCULAR LENS

CROSS REFERENCE TO RELATED APPLICATIONS

This is a continuation in part application designating US of International Application PCT/CN2017/109294, filed on Nov. 3, 2017, which is based upon and claims priority to Chinese Patent Application No. CN201710566074.5, filed on Jul. 12, 2017, the entire contents of which are incorporated herein by reference.

TECHNICAL FIELD

The present invention relates to the technical field of intraocular lens, and in particular to a multifocal intraocular lens made by changing the optical surface structure of an optical zone.

BACKGROUND

The natural lens in the eye of a newborn baby is a colorless, transparency, and very soft lens. The ability of the natural lens of newborn baby's eye to change shape and produce dramatic changes in focus is magnificent. As a person ages, the change of external conditions, such as ultraviolet light exposure, the natural lens becomes less clear, more rigid, more color, and functions more like a monofocal lens. When over fifty or sixty years, more than 30 percent of people's crystalline lens will turn yellow or brown or even cloudy. The cloudiness is called a cataract. When this happens, not only lost the accommodative function, but also blurred vision and sensitivity to light. The results will be trouble reading, driving, and less colors vivid when this happens, such natural lens (i.e., the cataract lens) will have to be replaced with an artificial intraocular lens to restore eyesight of the cataract patient.

A typical intraocular lens is comprised of an optical body and a supporting arm, particularly, the optical body focuses light onto the retina of your eye to enable the optical lens to see the object. The supporting arm is used to support the optical zone, so that the optical zone of the lens is at the center of the eye which can be focused effectively.

The optical zone and supporting arm of the intraocular lens can be made of the same material or can be made of different materials. The intraocular lens made of the same material is commonly referred to as a one-piece lens, while the intraocular lens made of different materials is commonly referred to as a three-piece lens, and examples thereof are reported in U.S. Pat. Nos. 4,997,442 and 5,217,491, among these patents, the optical zones are both made of relatively soft optical materials and arm zone are both made of relatively hard materials.

The conventional monofocal intraocular lens can provide vision correction with a conventional distance, but cannot provide an effective adjustable-focus vision correction, besides, the design wavelength is always the detection wavelength, and chromatic aberration cannot be corrected within the visible light range. In other words, it cannot play a role of vision correction both at far and close distances. The only way to make the monofocal intraocular lens work both at far and close distances is to wear a pair of glasses. Another choice is to replace the cataract lens with a multifocal intraocular lens, to make vision at far, close and medium distances available. However, only a part of light at each distance is focused onto the retina of your eye, in addition, multifocal intraocular lens will have some other side effects exist. As a result, people begin to design a novel adjustable-focus intraocular lens, as disclosed in U.S. Pat. Nos. 4,409,691, 5,674,282, 5,496,366, 6,197,059, and 6,387,126, 6,178,878, and 6,406,494. In an accommodating IOL, the loops are designed to keep the IOL securely in place and prevent any rotational movement, but the legs are flexible in a way that allows the optical portion of the IOL to move slightly forward upon contraction of the ciliary muscle. In this fashion, an accommodating IOL can expand the range of clear vision after cataract surgery, providing better near vision without eyeglasses than what is possible with a conventional monofocal IOL procedure. The optical portion of the IOL to move forward and backward distance is heavily rely on the contraction of the ciliary muscle. For some patients, the contraction of the ciliary muscle is too weak, cannot move the optical body of the intraocular lens, the intraocular lens turn to be the conventional monofocal intraocular lens. And also, the accommodative function will turn to weak along with the increase of the implantation time.

All the designed accommodative intraocular lenses are made of a soft silicone material with a low refractive index. Due to the fact of lower the refractive index of the silicone material, the intraocular lens made from it, is relatively thick, the intraocular lens has a limited distance to move within the capsular bag of your eye, resulted some focusing power back to the ageing eye, but will certainly not restore the same level of focusing available in a young person's eye. And also, the intraocular lens made from the silicone material will have a higher possibility to form fibers and secondary cataract than the intraocular lens made from hydrophobic polyacrylic ester material. Therefore, after the adjustable-focus lens made of silicone is implanted into the eye, only a part of people can have the adjustable-focus function, and the percentage of the part of people in the total number of transplanted people is also reduced along with the increase of the implantation time.

SUMMARY

In view of the problems existed in the prior art, the applicant provides a multifocal intraocular lens. The optical body of the present invention is a multifocal optical zone with a double-cemented structure. The optical zone includes a plurality of binary surfaces (two to four) and an aspheric surface, which can effectively correct chromatic aberration of the secondary spectrum, improve image quality, expand the range of additional optical power, and achieve a full range of vision.

Technical solutions of the present invention are as follows:

A multifocal intraocular lens, including an optical body, a first support loop) and a second support loop, wherein, the optical body is composed of a substrate layer and a coating layer; the substrate layer, the first support loop and the second support loop have a one-piece structure and are formed integrally with the same material;

the coating layer is cemented on the substrate layer by means of injection-compression molding; the substrate layer and the coating layer) are made of different materials.

Surfaces of the first support loop and the second support loop are both provided with oblique serration groove or protrusion frost; the roughness of the frost or the height of the oblique serration is greater than 40 μm.

The optical body has four optical surfaces in the optical axis direction, that is, optical surfaces (a), (b), (c), (d), respectively, wherein the optical surface (a) is close to the cornea, the optical surface (d) is close to the retina, and the optical surfaces (b) and (c) are coincident, but are located on different materials in the front and back, the optical surface (b) is attached to the back side of the base layer, the optical surface (c) is attached to the front side of the coating layer, at least two of the four optical surfaces are selected to be processed into a diffractive surface having an embossed structure, and the remaining optical surfaces are processed into aspherical surfaces.

The diffractive surface having an embossed structure is designed by the following methods:

$$\phi(r)=2\pi\alpha p[j-r^2/(2p\lambda_0 F_0)]$$

$$\alpha=\lambda/\lambda_0[n(\lambda)-n'(\lambda)]/[n(\lambda_0)-n'(\lambda_0)]$$

the formulas above describe a radius-based phase distribution function, wherein, $\lambda_0$ is the design wavelength, $\lambda$ is the wavelength of the actual incident light, $F_0$ is the focal length, n is the refractive index of the material, n' is the refractive index of the surrounding medium, j represents the j-th diffractive annular zone;
meanwhile, the step height of the serrated diffraction peak is given by the formula:

$$h_{max}(r)=p\lambda_0/[n(\lambda_0)-n'(\lambda_0)]$$

the phase function and the step height are roughly calculated from each focal length of the pre-designed multifocal points, an initial model is constructed in Zemax, and in turn optimized to obtain the best expected effect.

The structure of the aspherical surface is designed by the following methods:
taking the vertex of the optical surface as the origin O and the optical axis as the Z axis, an arbitrary space rectangular coordinate system is established, the abscissa axis X and coordinate axis Y axis of the coordinate system are tangential to the optical surface, and the surface shape of the aspheric surface satisfies an aspheric equation on the XZ plane of:

$$Z(x) = \frac{cy^2}{1+\sqrt{1-(1+Q)c^2y^2}} + \sum_{i=m}^{n} A_{2i}y^{2i}$$

wherein, Z(x) is a curve expression of the aspheric surface on the two-dimensional coordinate system plane XZ, c is the reciprocal of the basic spherical curvature radius of the aspheric surface, and y is a vertical distance from any point on the curve to the abscissa axis Z, $A_{2i}$ is the aspheric high-order coefficient, m and n are both integers not less than 1, and n>m, Q is an aspherical coefficient.

The effective optical zone of the optical body (1) is 5.5 to 6.5 mm in diameter, and a biconvex/meniscus lens sheet with a central thickness of 0.65-1.25 mm; the thickness of the base layer is 0.43-0.83 mm; the thickness of the coating layer is 0.22-0.42 mm; the thicknesses of the first support loop and the second support loop are both 0.15-0.35 mm; the spherical aberration of the optical body is in the range of −0.1 μm~−0.2 μm; the additional optical power of the optical body is in the range of +2D-+4.75D.

The base layer is made of hydrophobic polyacrylic ester having a refractive index of 1.48~1.56 and a dispersion coefficient of 35-55; the coating layer is made of a silicone material having a refractive index of 1.36-1.47, hydrophilic acrylic having a lower refractive index or hydrophobic polyacrylic ester having a lower refractive index.

Surfaces of the first support loop and the second support loop are provided with several oblique serration grooves/protrusions, and the width of the oblique serration groove/protrusion is 0.2-1.0 mm, the included angle α between the oblique edge of the oblique serration and the plane to which the support loop belongs is between −20°-20°.

The multifocal intraocular lens in the present invention is prepared by design steps as follows.

A Optical design: the phase function and the step height are roughly calculated from each focal length of the pre-designed multifocal points, an initial model is constructed in Zemax, and in turn optimized to obtain the best expected effect, the optical system is confirmed and evaluated by analyzing a light focus drift diagram, a spot diagram, an OPD optical characteristics curve, an MTF curve and the like.

B Lathe processing of base layer: lathe programs are compiled according to designed parameters of the base layer—in the optical zone; optical surfaces (a) and (b) of the lens are lathed with single point diamond turning technology; milling machine programs are compiled to mill out the profile of optical zones and frosted/serrated loop.

C Preparation of a pressing mold: a prototype mold is manufactured by using single point diamond turning, laser etching is mainly used to modify a diffractive surface having an embossed structure (if necessary).

D Injection-compression molding: the finished base layer is placed into the groove of the fixture, an appropriate amount of the medical grade silicone material MED-6820 dropped in the center of the optical part, and a stamper is fixed on the base mold (locked by a mechanical structure), and taken out after being placed at a temperature of 50° C.-150° C. for 20 minutes to 24 hours, and a clear and elastic coating layer 1-2 is formed.

E Polishing

The multifocal intraocular lens can first be lathed out a film base containing an optical surface (a) and an optical surface (c), and the coating layer is tightly attached to the optical surface (b) of the base layer—by an injection molding process, the optical surface (c) is obtained by compression molding, and then an intraocular lens disk is made, and the optical body of the lens is mechanically engraved, and the two loops are made by mechanical cutting.

The base layer in the optical body of the present invention is made of an optically transparent hydrophobic polyacrylic ester material, which is an optically transparent acrylic copolymer obtained by copolymerizing acrylate, methacrylate and styrene derivatives (or small amounts of hydrophilic monomers) at a high temperature.

The coating layer in the optical body of the present invention is made of an optically transparent material having a lower refractive index, and the optically transparent material can be optically transparent medical grade silicone (such as Med 6820), a biocompatible optically transparent hydrophilic acrylic material or a biocompatible optically transparent hydrophobic polyacrylic ester material. The chemical linkage bonds of the base layer and the coating layer are formed under higher temperature condition.

The beneficial effects of the present invention lie in that: the optical zone of the optical body according to the present invention selectively matches two materials, combines an aspherical surface and a binary surface and realizes the elimination of color aberration in the visible light range, and has a greater focal depth and a better image quality.

The optical zone of the optical body in the present invention is an optical zone having two focal points, three focal points, or regional multifocal points; a double-cemented lens is made of two materials, two contact surfaces of the lens have a common curvature, dispersion characteristics of the two materials are different, after cementing, first-order chromatic aberration can be corrected. Combined with the technical design schemes, it can be seen from the polychromatic light focus drift diagram that the a parabolic drift diagram replaces the original straight line, because correcting of the chromatic aberration can obtain a better image quality; meanwhile, the optical body has at least two diffractive surfaces (2 to 4 diffractive surfaces), on the basis of the existing multi-focal technology, the additional optical power range (+2D-+4.75D) is widened, a full range of vision is achieved, chromatic aberration of the secondary spectrum is further eliminated on the basis of correcting the first-order chromatic aberration; the roles of the aspheric surface are to control the spherical aberration, adjust the depth of focus, and improve visual quality; the optical body is formed by accurate injection-compression molding, with a high efficiency (to compress one mould only takes 5-10 seconds) and a high accuracy. This process is applied to processing of a diffractive surface intraocular lens for the first time, and metal or polyimide (PI) matrix composite material mold is adopted, the mold can be processed with laser direct writing or etching technology, and having a higher precision than that with single point diamond turning technology.

The cementing process and the condensation process after compression molding process have strict requirements on the environment temperature and humidity, so that the stress matching between the two materials is guaranteed, and the lens can be suitable for a complex eye-liquid environment; finally, the design of the frosted/serrated surface of the support loop increases the resistance of movement of the loop, preventing the lens from rotating in the capsular bag, and improving the stability after the surgery.

In the figures: 1. Optical body, 1-1. Base layer, 1-2. Coating layer, 2. First support loop, 3. Second support loop, a, b, c and d: four optical surfaces of the optical body.

DETAILED DESCRIPTION OF THE INVENTION

The present invention will be described in detail in conjunction with the accompanying drawings and embodiments.

Embodiment 1

Figure 1:
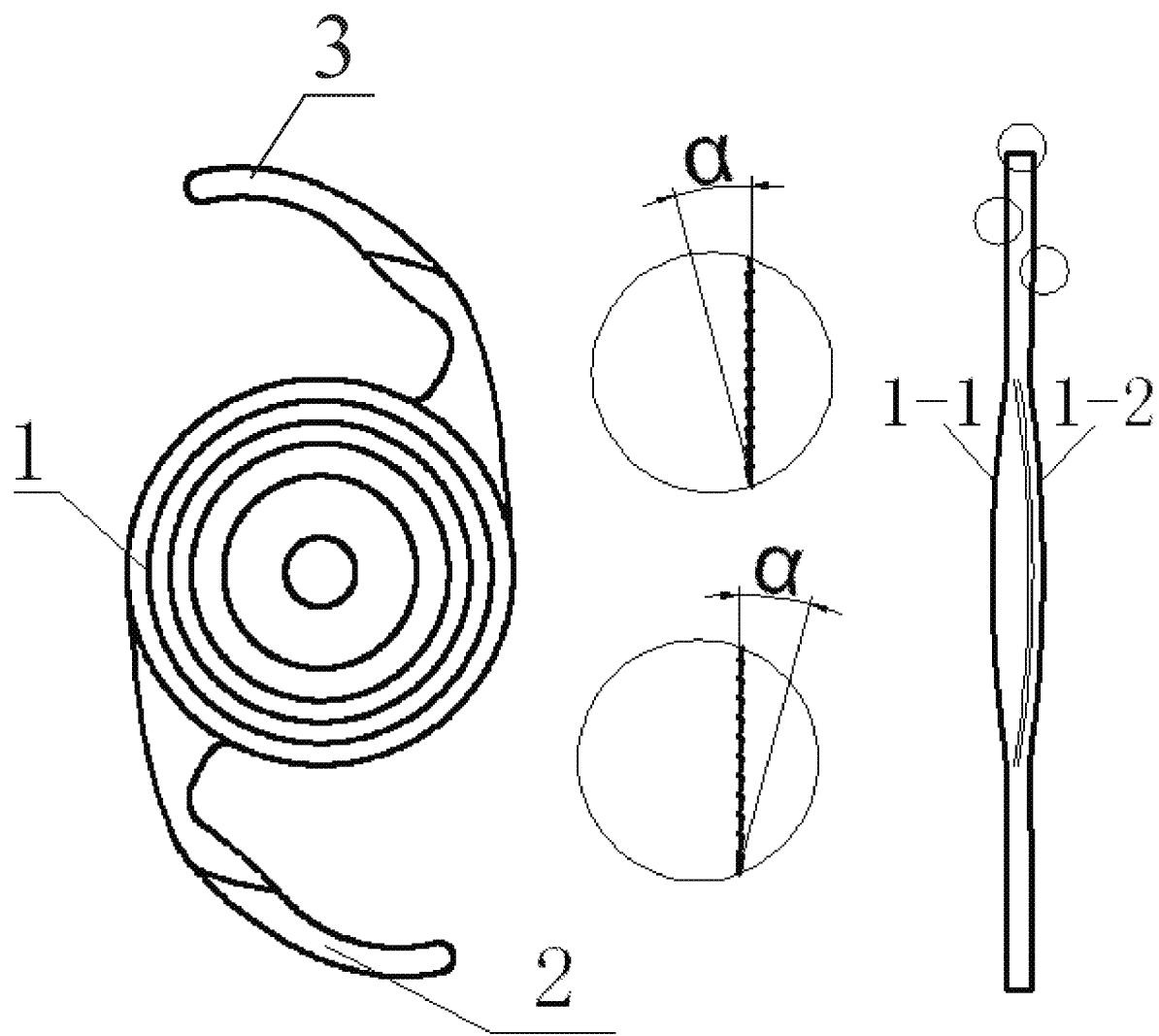
FIG. 1 is a schematic structural diagram according to Embodiment 1 of the present invention.

As shown in FIG. 1, a multifocal intraocular lens, including an optical body 1, a first support loop 2 and a second support loop 3, wherein, the optical body 1 is composed of a substrate layer 1-1 and a coating layer 1-2;

the substrate layer 1-1, the first support loop 2 and the second support loop 3 have a one-piece structure and are formed integrally with the same material.

The coating layer 1-2 is cemented on the substrate layer 1-1 by means of injection-compression molding;

the substrate layer 1-1 and the coating layer 1-2 are made of different materials.

Surfaces of the first support loop 2 and the second support loop 3 are both provided with oblique serration groove; the height of the oblique serration is greater than 40 μm.

The optical body 1 has four optical surfaces in the optical axis direction, that is, optical surfaces a, b, c, d, respectively, wherein the optical surface a is close to the cornea, the optical surface d is close to the retina, and the optical surfaces b and c are coincident, but are located on different materials in the front and back, the optical surface b is attached to the back side of the base layer 1-1, the optical surface c is attached to the front side of the coating layer 1-2.

The effective optical zone of the optical body 1 is 5.5 mm in diameter, and a biconvex lens sheet with a central thickness of 0.65 mm; the thickness of the base layer 1-1 is 0.43 mm;

the thickness of the coating layer 1-2 is 0.22 mm; the thicknesses of the first support loop 2 and the second support loop 3 are both 0.15 mm;

the base layer 1-1 is made of hydrophobic polyacrylic ester having a refractive index of 1.544 and a dispersion coefficient of 35~55; the coating layer 1-2 is made of a silicone material having a refractive index of 1.41, or hydrophilic acrylic having a lower refractive index.

Surfaces of the first support loop 2 and the second support loop 3 are provided with several oblique serration grooves, and the width of the oblique serration groove is 0.2 mm, the included angle α between the oblique edge of the oblique serration and the plane to which the support loop belongs is between −20°-20°.

The preparation method of the multifocal intraocular lens is as follows.

Figure 4:
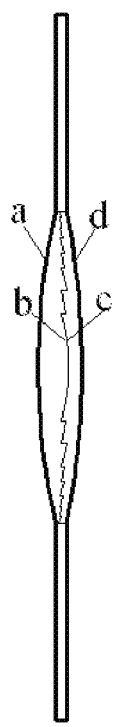
FIG. 4 is a side view of an optical part according to Embodiment 1 of the present invention, wherein optical surfaces b and c are diffractive surfaces.

(1) The design scheme: optical surfaces b and c of the optical body are diffractive surfaces, optical surfaces a and d are aspheric surfaces, the additional optical power is 3.5D; the side view of the optical part is as shown in FIG. 4.

Figure 7:
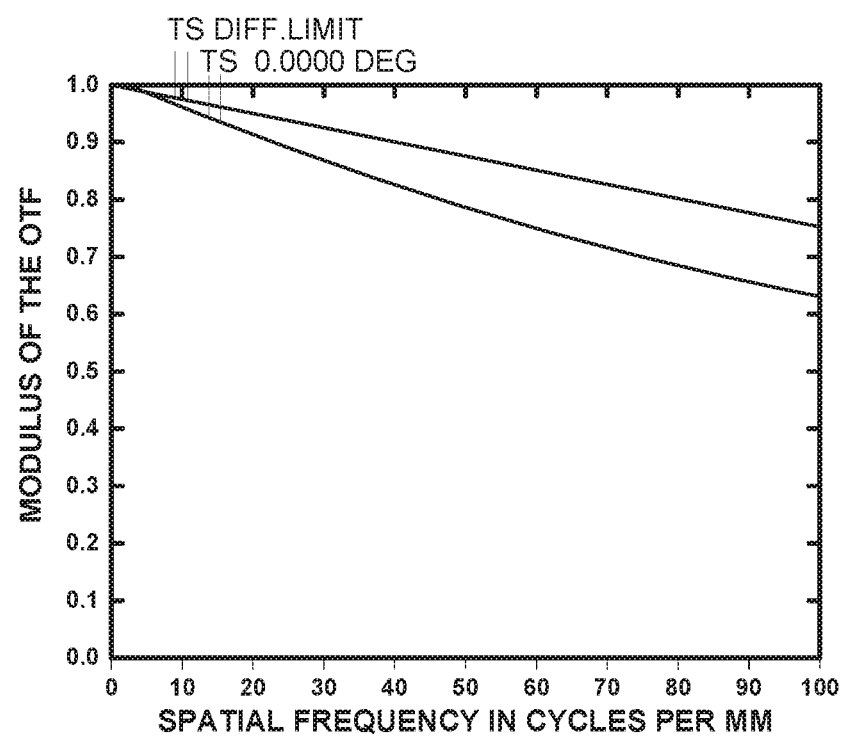
FIG. 7 is a distribution diagram of a far-focus MTF of the optical body along with the spatial frequence according to Embodiment 1 of the present invention.
Figure 8:
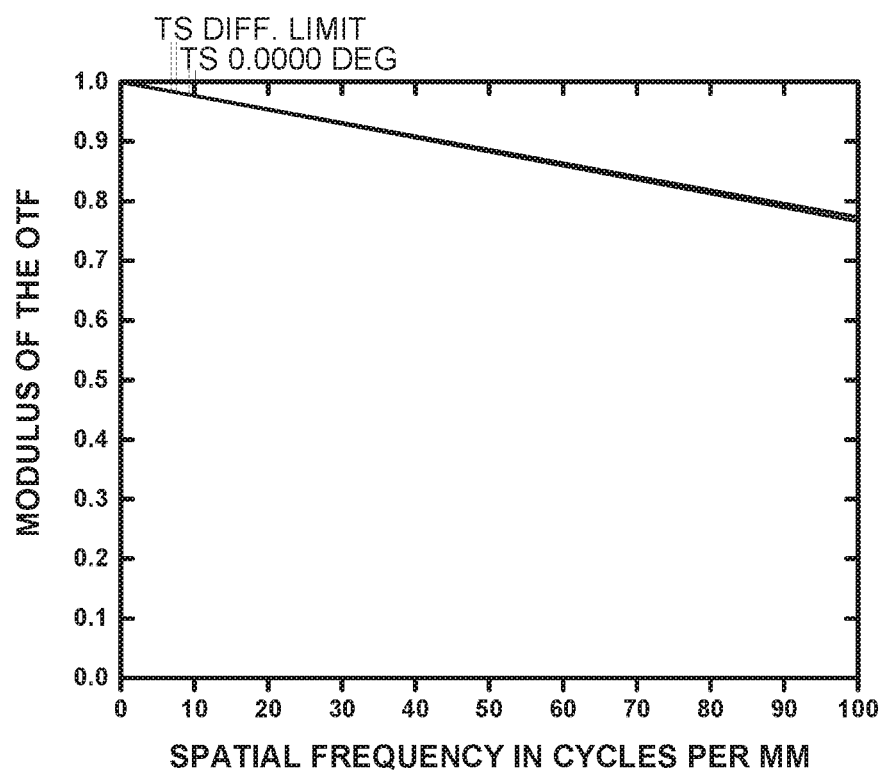
FIG. 8 is a distribution diagram of an intermediate-focus MTF of the optical body along with the spatial frequence according to Embodiment 1 of the present invention.
Figure 9:
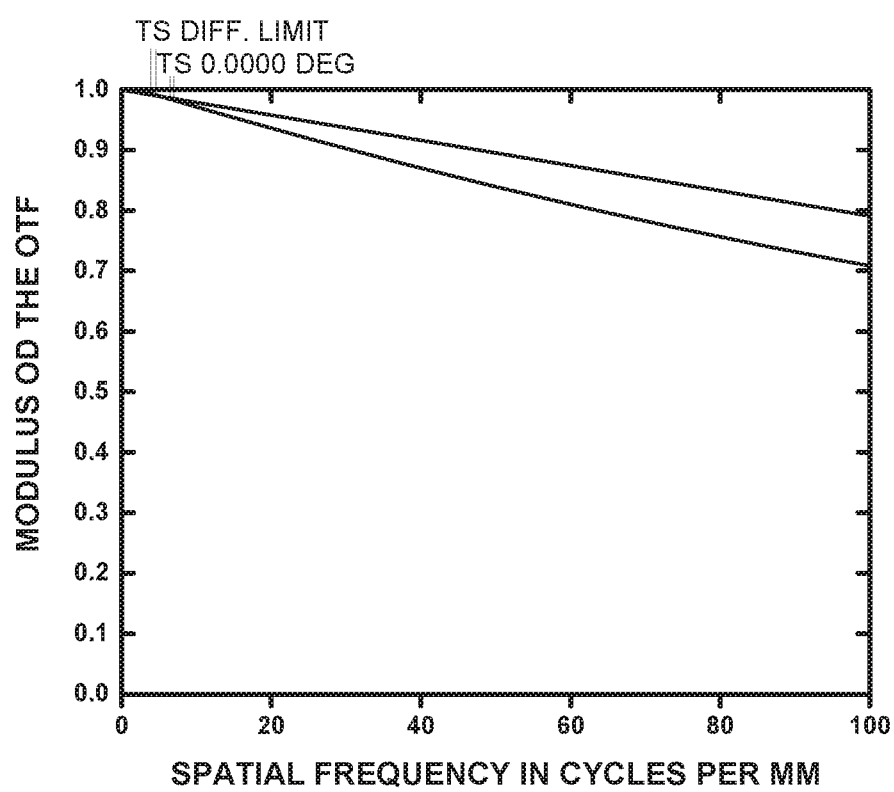
FIG. 9 is a distribution diagram of a near-focus MTF of the optical body along with the spatial frequence according to Embodiment 1 of the present invention.

(2) The Optical design: the phase function and the step height are roughly calculated from each focal length of the pre-designed multifocal points, i.e., 17.59 mm (21.5D), 19.38 mm (19.5D), 20.99 mm (18D), an initial model is constructed in Zemax, and in turn optimized to obtain the best expected effect, the optical system is confirmed and evaluated by analyzing a MTF curve. The evaluation results are as shown in FIG. 7, FIG. 8 and FIG. 9, as can be seen from the figures, MTFs of the three focuses are all above 0.43 from wavelength of 486 nm to 656 nm (at a dominant wavelength (a at a spatial frequence of 100 lp/mm in an eye model) without taking into account the diffraction efficiency of each focus. The image quality meets the requirements of national standards, and a certain additional focal power is provided.

(3) Lathe processing of base layer: lathe programs are compiled according to designed parameters of the base layer 1-1 in the optical zone; optical surfaces a and b of the lens are lathed with single point diamond turning technology; milling machine programs are compiled to mill out the profile of optical zones and frosted loop.

(4) Preparation of a pressing mold: a prototype mold is manufactured by using single point diamond turning, laser etching is mainly used to modify a diffractive surface having an embossed structure (if necessary).

(5) The preparation of silicone materials: 10 ml of each of silicone materials (MED-6820) PART A and PART B is taken into a glass beaker, with stirring by a glass rods for at least 2 minutes until the silicone materials become completely homogeneous, stand in vacuum or at a low temperature until bubbles are completely removed.

(6) Injection-compression molding: the finished base layer 1-1 is placed into the groove of the fixture, an approximate 0.5 ml of the silicone material is dropped into the center of the optical part, and a stamper is fixed on the base mold (locked by a mechanical structure), and taken out after being placed at a temperature of 50° C. for 24 hours to be completely cured silicone material.

(7) Finally, polishing processing is performed to obtain an intraocular lens with qualified optical surfaces.

Embodiment 2

Figure 2:
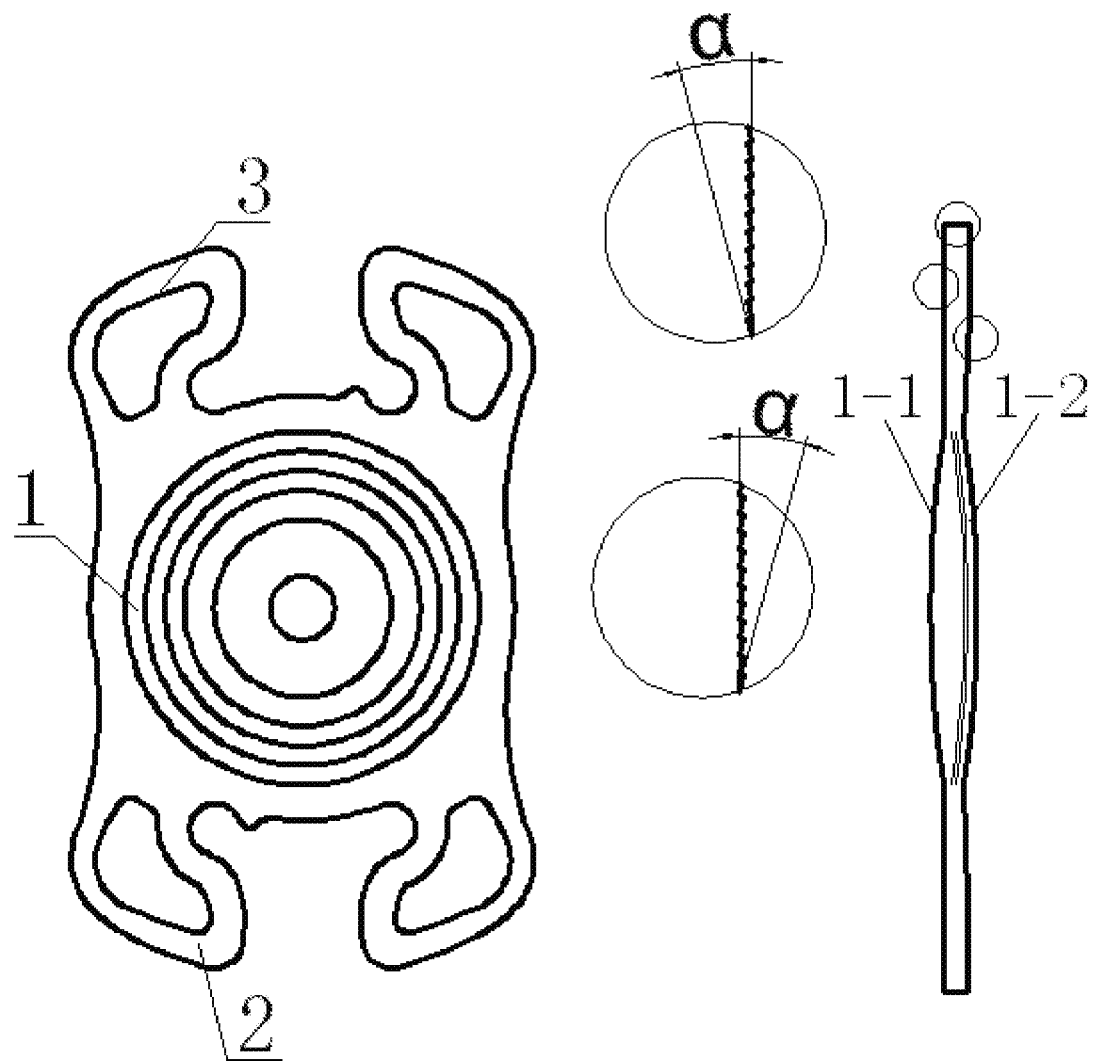
FIG. 2 is a schematic structural diagram according to Embodiment 2 of the present invention.

As shown in FIG. 2, a multifocal intraocular lens, including an optical body 1, a first support loop 2 and a second support loop 3, wherein, the optical body 1 is composed of a substrate layer 1-1 and a coating layer 1-2;
the substrate layer 1-1, the first support loop 2 and the second support loop 3 have a one-piece structure and are formed integrally with the same material.
the coating layer 1-2 is cemented on the substrate layer 1-1 by means of injection-compression molding;
the substrate layer 1-1 and the coating layer 1-2 are made of different materials.

The surfaces of the first support loop 2 and the second support loop 3 are both provided with protrusion frost; the height of the frost is greater than 40 μm.

The optical body 1 has four optical surfaces in the optical axis direction, that is, optical surfaces a, b, c, d, respectively, wherein the optical surface a is close to the cornea, the optical surface d is close to the retina, and the optical surfaces b and c are coincident, but are located on different materials in the front and back, the optical surface b is attached to the back side of the base layer 1-1, the optical surface c is attached to the front side of the coating layer 1-2.

The effective optical zone of the optical body 1 is 6.0 mm in diameter, and a meniscus lens sheet with a central thickness of 0.95 mm; the thickness of the base layer 1-1 is 0.65 mm;
the thickness of the coating layer 1-2 is 0.3 mm; the thicknesses of the first support loop 2 and the second support loop 3 are both 0.25 mm;
the spherical aberration of the optical body 1 is −0.1 μm; the additional optical power of the optical body 1 is in the range of +4.0D.

The base layer 1-1 is made of hydrophobic polyacrylic ester having a refractive index of 1.547 and a dispersion coefficient of 35-55; the coating layer 1-2 is made of hydrophilic acrylic having a refractive index of 1.362.

The surfaces of the first support loop 2 and the second support loop 3 are provided with several frosted protrusions, and the width of the frosted protrusion is 0.2 mm.

The preparation method of the multifocal intraocular lens is as follows.

Figure 5:
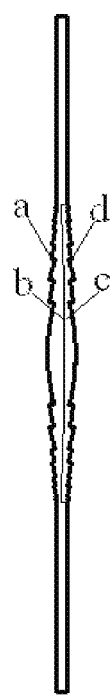
FIG. 5 is a side view of an optical part according to Embodiment 2 of the present invention, wherein optical surfaces a and d are diffractive surfaces.
Figure 6:
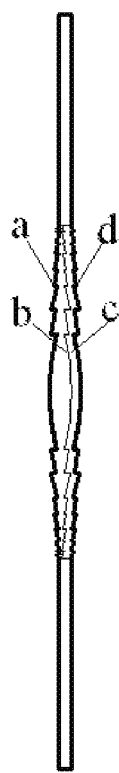
FIG. 6 is a side view of an optical part according to Embodiment 3 of the present invention, wherein optical surfaces a, b, c and d are diffractive surfaces.

(1) The design scheme: the optical surfaces a and d of the optical body are diffractive surfaces, the optical surfaces b and c are aspheric surfaces, the additional optical power is 4.0D; the side view of the optical part is as shown in FIG. 5.

(2) The optical design: the phase function and the step height are roughly calculated from each focal length of the pre-designed multifocal points, i.e., 17.59 mm (21.5D), 19.38 mm (19.5D), 21.41 mm (17.5D), an initial model is constructed in Zemax, and in turn optimized to obtain the best expected effect, the optical system is confirmed and evaluated by analyzing a light focus drift diagram, a spot diagram, an OPD optical characteristics curve, a through-focus MTF curve and the like.

(3) Lathe processing of base layer: lathe programs are compiled according to designed parameters of the base layer 1-1 in the optical zone; optical surfaces a and b of the lens are lathed with single point diamond turning technology; milling machine programs are compiled to mill out the profile of optical zones and frosted loop.

(4) The preparation of a pressing mold: a prototype mold is manufactured by using single point diamond turning, laser etching is mainly used to modify a diffractive surface having an embossed structure (if necessary).

(5) Preparation of hydrophilic materials: 10 ml of each of hydrophilic materials PART A and PART B is taken and put in a glass beaker, with stirring by a glass rods for at least 2 minutes until the hydrophilic materials become completely homogeneous, stand in vacuum or at a low temperature until bubbles are completely removed.

(6) Injection-compression molding: the finished base layer 1-1 is placed into the groove of the fixture, 0.5 ml of hydrophilic acrylic mixed solution is dropped into the center of the optical part, and a stamper is fixed on the base mold (locked by a mechanical structure), and taken out after being placed at a temperature of 100° C. for 12 hours to be completely cured.

(7) Finally, polishing processing is performed to obtain a qualified intraocular lens.

Embodiment 3

Figure 3:
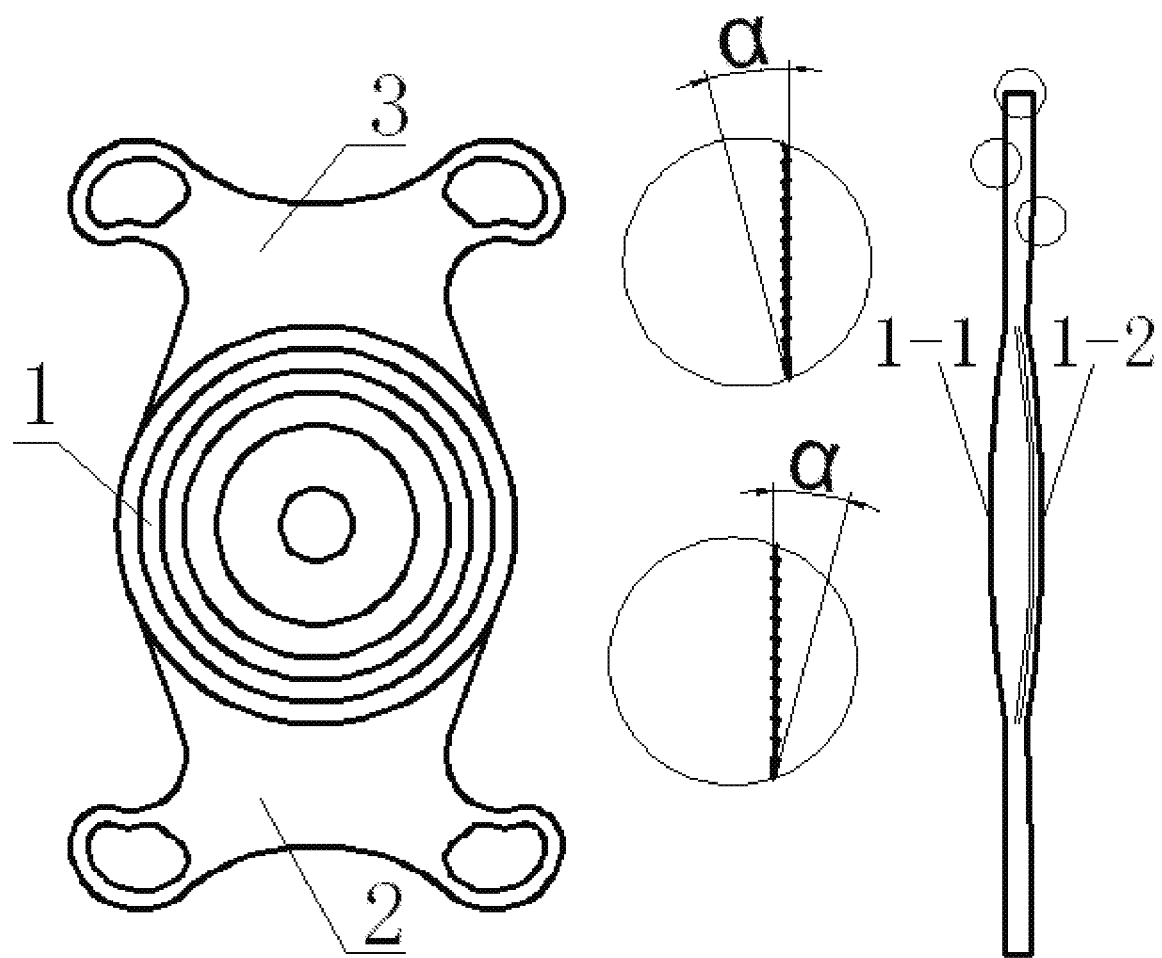
FIG. 3 is a schematic structural diagram according to Embodiment 3 of the present invention.

As shown in FIG. 3, a multifocal intraocular lens, including an optical body 1, a first support loop 2 and a second support loop 3, wherein, the optical body 1 is composed of a substrate layer 1-1 and a coating layer 1-2;
the substrate layer 1-1, the first support loop 2 and the second support loop 3 have a one-piece structure and are formed integrally with the same material.
The coating layer 1-2 is cemented on the substrate layer 1-1 by means of injection-compression molding;
the substrate layer 1-1 and the coating layer 1-2 are made of different materials.

The surfaces of the first support loop 2 and the second support loop 3 are both provided with an oblique serration groove; the height of the oblique serration is greater than 40 μm.

The optical body 1 has four optical surfaces in the optical axis direction, that is, optical surfaces a, b, c, d, respectively, wherein the optical surface a is close to the cornea, the optical surface d is close to the retina, and the optical surfaces b and c are coincident, but are located on different materials in the front and back, the optical surface b is attached to the back side of the base layer 1-1, the optical surface c is attached to the front side of the coating layer 1-2.

The effective optical zone of the optical body 1 is 6.5 mm in diameter, and a biconvex lens sheet with a central thickness of 1.25 mm; the thickness of the base layer 1-1 is 0.83 mm; the thickness of the coating layer 1-2 is 0.42 mm; the thicknesses of the first support loop 2 and the second support loop 3 are both 0.35 mm;

the spherical aberration of the optical body 1 is −0.2 μm; the additional optical power of the optical body 1 is in the range of +4.5D.

The base layer 1-1 is made of hydrophobic polyacrylic ester having a refractive index of 1.542 and a dispersion coefficient of 35~55; the coating layer 1-2 is made of hydrophilic acrylic having a refractive index of 1.462.

The surfaces of the first support loop 2 and the second support loop 3 are provided with several oblique serration grooves, and the width of the oblique serration groove is 0.8 mm, the included angle α between the oblique edge of the oblique serration and the plane to which the support loop belongs is 15°.

The preparation method of the multifocal intraocular lens is as follows.

(1) The design scheme: optical surfaces a, b, c and d of the optical body are diffractive surfaces, and the additional optical power is 4.5D; the side view of the optical part is as shown in FIG. 5.

(2) The optical design: the phase function and the step height are roughly calculated from each focal length of the pre-designed multifocal points, i.e., 16.97 mm (22.0D), 19.38 mm (19.5D), 21.41 mm (17.5D), an initial model is constructed in Zemax, and in turn optimized to obtain the best expected effect, the optical system is confirmed and evaluated by analyzing a light focus drift diagram, a spot diagram, an OPD optical characteristics curve, a through-focus MTF curve and the like.

(3) Lathe processing of base layer: lathe programs are compiled according to designed parameters of the base layer 1-1 in the optical zone; optical surfaces a and b of the lens are lathed with single point diamond turning technology; milling machine programs are compiled to mill out the profile of optical zones and serrated loop.

(4) The preparation of a pressing mold: a prototype mold is manufactured by using single point diamond turning, laser etching is mainly used to modify a diffractive surface having an embossed structure (if necessary), and the surface accuracy is detected with a high precision profiler.

(5) The preparation of hydrophobic materials: 10 ml of each of hydrophobic materials PART A and PART B is taken and put in a glass beaker, with stirring by a glass rods for at least 2 minutes until the hydrophobic materials become completely homogeneous stand in vacuum or at a low temperature until bubbles are completely removed.

(6) Injection-compression molding: the finished base layer 1-1 is dropped into the groove of the fixture, 0.5 ml of hydrophobic polyacrylic ester mixed solution is dropped into the center of the optical part, and a stamper is fixed on the base mold (locked by a mechanical structure), and taken out after being placed at a temperature of 50° C. for 24 hours to be completely cured.

(7) Finally, polishing processing is performed to obtain a qualified intraocular lens.

What is claimed is:

1. A multifocal intraocular lens comprising:
   an optical body, a first support loop, and a second support loop;

wherein, the optical body comprises a substrate layer and a coating layer;
   the substrate layer, the first support loop and the second support loop have a one-piece structure and are formed integrally with a same material;
   the coating layer is cemented on the substrate layer by means of injection-compression molding;
   the substrate layer and the coating layer are made of different materials;
   and wherein the optical body has four optical surfaces in an optical axis direction including a first optical surface, a second optical surface, a third optical surface, and a fourth optical surface respectively;
   the first optical surface is close to the cornea, the fourth optical surface is close to the retina, the second and third optical surfaces are coincident but are located on different materials in the front and back, the second optical surface is attached to a back side of a base layer, the third optical surface is attached to a front side of the coating layer, at least two of the four optical surfaces are selected to be processed into a diffractive surface having an embossed structure, and remaining optical surfaces are processed into aspherical surfaces;
   and wherein the diffractive surface having an embossed structure is designed by calculating a radius-based phase distribution function and a step height of a serrated diffraction peak from each focal length of pre-designed multifocal points according to the following formulas, $$\phi(r) = 2\pi\alpha p[j - r^2/(2p\lambda_0 F_0)]$$

$$\alpha = \lambda/\lambda_0[n(\lambda) - n'(\lambda)]/[n(\lambda_0) - n'(\lambda_0)]$$

the formulas above describe the radius-based phase distribution function, wherein, $\lambda_0$ is a design wavelength, $\lambda$ is a wavelength of actual incident light, $F_0$ is a focal length, n is a refractive index of a material, n' is a refractive index of a surrounding medium, j represents a j-th diffractive annular zone;
   a step height of a serrated diffraction peak is given by the formula below:

$$h_{max}(r) = p\lambda_0/[n(\lambda_0) - n'(\lambda_0)]$$

after the calculation, an initial model is constructed in an optical design software, and then the initial model is optimized to obtain the best expected effect.

2. The multifocal intraocular lens according to claim 1, wherein
   a diameter of the effective optical zone of the optical body ranges from 5.5 mm to 6.5 mm and has a central thickness that ranges from 0.65 mm to 1.25 mm;
   a thickness of the base layer ranges from 0.43 mm to 0.83 mm;
   a thickness of the coating layer ranges from 0.22 mm to 0.42 mm; and
   a thicknesses of the first support loop and the second support loop ranges from 0.15 mm to 0.35 mm.

3. The multifocal intraocular lens according to claim 1, wherein
   a spherical aberration of the optical body ranges from −0.1 μm to −0.2 μm; and
   an optical power of the optical body ranges from +2D to +4.75D.

4. The multifocal intraocular lens according to claim 1, wherein
   the base layer is made of hydrophobic polyacrylic ester having a refractive index ranges from 1.48 to 1.56 and a dispersion coefficient ranges from 35 to 55;

the coating layer is made of a silicone material having a refractive index ranges from 1.36 to 1.47 and hydrophilic acrylic having a lower refractive index or hydrophobic polyacrylic ester having a lower refractive index.

5. The multifocal intraocular lens according to claim 1, wherein surfaces of the first support loop and the second support loop are provided with at least one oblique serration groove or protrusion, and a width of the oblique serration groove or protrusion ranges from 0.2 mm to 1.0 mm; and an included angle between an oblique edge of the oblique serration and a plane of the first or second support loop is between −20° and 20°.

6. A multifocal intraocular lens comprising:

an optical body, a first support loop, and a second support loop;

wherein, the optical body comprises a substrate layer and a coating layer;

the substrate layer, the first support loop and the second support loop have a one-piece structure and are formed integrally with a same material;

the coating layer is cemented on the substrate layer by means of injection-compression molding;

the substrate layer and the coating layer are made of different materials;

and wherein the optical body has four optical surfaces in an optical axis direction including a first optical surface, a second optical surface, a third optical surface, and a fourth optical surface respectively;

the first optical surface is close to the cornea, the fourth optical surface is close to the retina, the second and third optical surfaces are coincident but are located on different materials in the front and back, the second optical surface is attached to a back side of a base layer, the third optical surface is attached to a front side of the coating layer, at least two of the four optical surfaces are selected to be processed into a diffractive surface having an embossed structure, and remaining optical surfaces are processed into aspherical surfaces;

and wherein the structure of the aspherical surface is designed by taking a vertex of one optical surface as an origin and an optical axis as the Z axis to establish an arbitrary space rectangular coordinate system, the abscissa axis X and coordinate axis Y axis of the arbitrary space rectangular coordinate system are tangential to the optical surface, and a surface shape of the aspheric surface satisfies an aspheric equation on the XZ plane of:

$$Z(x) = \frac{cy^2}{1 + \sqrt{1-(1+Q)c^2y^2}} + \sum_{i=m}^{n} A_{2i} y^{2i}$$

wherein, $Z(x)$ is a curve expression of the aspheric surface on a two-dimensional coordinate system plane XZ, c is a reciprocal of a basic spherical curvature radius of the aspheric surface, and y is a vertical distance from any point on the curve to the abscissa axis Z, $A_{2i}$ is an aspheric high-order coefficient, m and n are both integers not less than 1, and n>m, Q is an aspherical coefficient.

7. The multifocal intraocular lens according to claim 6, wherein a diameter of the effective optical zone of the optical body ranges from 5.5 mm to 6.5 mm and has a central thickness that ranges from 0.65 mm to 1.25 mm;

a thickness of the base layer ranges from 0.43 mm to 0.83 mm;

a thickness of the coating layer ranges from 0.22 mm to 0.42 mm; and a thicknesses of the first support loop and the second support loop ranges from 0.15 mm to 0.35 mm.

8. The multifocal intraocular lens according to claim 6, wherein a spherical aberration of the optical body ranges from −0.1 μm to −0.2 μm; and an optical power of the optical body ranges from +2D to +4.75D.

9. The multifocal intraocular lens according to claim 6, wherein the base layer is made of hydrophobic polyacrylic ester having a refractive index ranges from 1.48 to 1.56 and a dispersion coefficient ranges from 35 to 55;

the coating layer is made of a silicone material having a refractive index ranges from 1.36 to 1.47 and hydrophilic acrylic having a lower refractive index or hydrophobic polyacrylic ester having a lower refractive index.

10. The multifocal intraocular lens according to claim 6, wherein surfaces of the first support loop and the second support loop are provided with at least one oblique serration groove or protrusion, and a width of the oblique serration groove or protrusion ranges from 0.2 mm to 1.0 mm; and an included angle between an oblique edge of the oblique serration and a plane of the first or second support loop is between −20° and 20°.

\* \* \* \* \*